(12) United States Patent
Simmonds et al.

(10) Patent No.: US 6,927,570 B2
(45) Date of Patent: *Aug. 9, 2005

(54) METHOD AND APPARATUS FOR MAKING MEASUREMENTS OF ACCUMULATIONS OF MAGNETICALLY SUSCEPTIBLE PARTICLES COMBINED WITH ANALYTES

(75) Inventors: Michael Bancroft Simmonds, Mammoth Lakes, CA (US); Kurt Gordon Jensen, Poway, CA (US); Jost Hermann Diederichs, Poway, CA (US); Randall Christopher Black, San Diego, CA (US)

(73) Assignee: Quantum Design, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/625,720

(22) Filed: Jul. 22, 2003

(65) Prior Publication Data

US 2004/0150396 A1 Aug. 5, 2004

Related U.S. Application Data

(63) Continuation of application No. 09/911,934, filed on Jul. 23, 2001, now Pat. No. 6,597,176, which is a division of application No. 09/451,660, filed on Nov. 30, 1999, now Pat. No. 6,437,563, which is a continuation-in-part of application No. 08/975,569, filed on Nov. 21, 1997, now Pat. No. 6,046,585.

(51) Int. Cl.$^7$ .......................... G01N 27/72; G01N 27/74
(52) U.S. Cl. ...................... 324/239; 324/204; 324/71.4; 324/226; 422/68.1; 436/526
(58) Field of Search .................................. 324/201, 204, 324/225, 226, 237, 71.4, 232–234, 236, 243, 239; 422/68.1; 436/526

(56) References Cited

U.S. PATENT DOCUMENTS

| | | | | |
|---|---|---|---|---|
| 4,875,357 A | * | 10/1989 | Giallorenzi | 356/437 |
| 5,512,822 A | * | 4/1996 | Masuda | 324/235 |
| 6,051,970 A | * | 4/2000 | Hutchings | 324/204 |
| 6,552,530 B1 | * | 4/2003 | Vaiser et al. | 324/204 |

* cited by examiner

Primary Examiner—Jay Patidar
(74) Attorney, Agent, or Firm—Mark D. Wieczorek, Esq.

(57) ABSTRACT

An apparatus is provided for quantitatively measuring samples whose amount or other characteristic quality is to be determined. The samples are arranged in a predefined pattern and are excited in a magnetic field. The magnetizations of the magnetic particles are thereby caused to oscillate at the excitation frequency in the manner of a dipole to create their own fields. These fields are inductively coupled to at least one substantially flat sensor such as sensing coils fabricated in a gradiometer configuration.

1 Claim, 7 Drawing Sheets

Position of Spot with Respect to Sense Coils

METHOD AND APPARATUS FOR MAKING MEASUREMENTS OF ACCUMULATIONS OF MAGNETICALLY SUSCEPTIBLE PARTICLES COMBINED WITH ANALYTES

CROSS REFERENCE TO RELATED APPLICATIONS

This is a continuation application of U.S. patent application Ser. No. 09/911,934 filed on Jul. 23, 2001 now U.S. Pat. No. 6,597,176, entitled "Method And Apparatus For Making Measurements Of Patterns Of Magnetic Particles In Lateral Flow Membranes And Microfluidic Systems" which is a divisional patent application of U.S. patent application Ser. No. 09/451,660 filed on Nov. 30, 1999, now U.S. Pat. No. 6,437,563 entitled "Method and Apparatus for Making Measurements of Accumulations of Magnetic Particles", which is a continuation-in-part patent application of U.S. patent application Ser. No. 08/975,569 filed on Nov. 21, 1997, now U.S. Pat. No. 6,046,585 entitled "Method and Apparatus for Making Quantitative Measurements of Localized Accumulations of Targets Particles Having Magnetic Particles Bound Thereto".

BACKGROUND OF THE INVENTION

1. Field of the Invention

This invention relates generally to sensing the presence of magnetic particles, and more particularly to quantitatively measuring accumulations of such particles by means of AC magnetic excitation and inductive sensing of the amplitude of the resulting oscillations of the magnetic moments of the particles at the excitation frequency.

2. Discussion of Prior Art

Much attention has been given to techniques for determining the presence, and possibly the level of concentration, of minute particles in a larger mixture or solution in which the particles reside. It is desirable in certain circumstances to measure very low concentrations of certain organic compounds. In medicine, for example, it is very useful to determine the concentration of a given kind of molecule, usually in solution, which either exists naturally in physiological fluids (for example, blood or urine) or which has been introduced into the living system (for example, drugs or contaminants).

One broad approach used to detect the presence of a particular compound of interest, referred to as the analyte, is the immunoassay, in which detection of a given molecular species, referred to generally as the ligand, is accomplished through the use of a second molecular species, often called the antiligand, or the receptor, which specifically binds to the first compound of interest. The presence of the ligand of interest is detected by measuring, or inferring, either directly or indirectly, the extent of binding of ligand to antiligand.

A discussion of several detection and measurement methods appears in U.S. Pat. No. 4,537,861 (Elings et al.). That patent discloses several ways to accomplish homogenous immunoassays in a solution of a binding reaction between a ligand and an antiligand, which are typically an antigen and an antibody. Elings discloses creation of a spatial pattern formed by a spatial array of separate regions of antiligand material and ligand material dispersed to interact with the spatial array of separate regions of antiligand material for producing a binding reaction between the ligand and the antiligand in the spatial patterns and with the bound complexes labeled with a particular physical characteristic. After the labeled bound complexes have been accumulated in the spatial patterns, the equipment is scanned to provide the desired immunoassay. The scanner may be based on fluorescence, optical density, light scattering, color and reflectance, among others.

The labeled bound complexes are accumulated on specially prepared surface segments according to Elings, or within an optically transparent conduit or container by applying localized magnetic fields to the solution where the bound complexes incorporate magnetic carrier particles. The magnetic particles have a size range of 0.01 to 50 microns. Once the bound complexes are accumulated magnetically within the solution, the scanning techniques previously described are employed.

Magnetic particles made from magnetite and inert matrix material have long been used in the field of biochemistry. They range in size from a few nanometers up to a few microns in diameter and may contain from 15% to 100% magnetite. They are often described as superparamagnetic particles or, in the larger size range, as beads. The usual methodology is to coat the surface of the particles with some biologically active material that causes them to bond strongly with specific microscopic objects or particles of interest (e.g., proteins, viruses, cells, DNA fragments). The particles then become "handles" by which the objects can be moved or immobilized using a magnetic gradient, usually provided by a strong permanent magnet. Thus, the Elings patent is an example of tagging using magnetic particles. Specially constructed fixtures using rare-earth magnets and iron pole pieces are commercially available for this purpose.

Although these magnetic particles have only been used in practice for moving or immobilizing the bound objects, some experimental work has been done on using the particles as tags for detecting the presence of the bound object. This tagging is usually done by radioactive, fluorescent, or phosphorescent molecules which are bound to the objects of interest. A magnetic tag, if detectable in sufficiently small amounts, would be very attractive because the other tagging techniques all have various important weaknesses. For example, radioactive methods present health and disposal problems. The methods are also relatively slow. Fluorescent or phosphorescent techniques are limited in their quantitative accuracy and dynamic range because emitted photons may be absorbed by other materials in the sample. See Japanese Patent Publication 63-90765, published Apr. 21, 1988 (Fujiwara et al.).

Because the signal from a very tiny volume of magnetic particles is exceedingly small, it has been natural that researchers have tried building detectors based on Superconducting Quantum Interference Devices ("SQUID"s). SQUID amplifiers are well known to be the most sensitive detectors of magnetic fields in many situations. There are several substantial difficulties with this approach, however. Since the pickup loops of the SQUID must be maintained at cryogenic temperatures, the sample must be cooled to obtain a very close coupling to these loops. This procedure makes the measurements unacceptably tedious. The general complexity of SQUIDs and cryogenic components renders them generally unsuitable for use in an inexpensive desktop instrument. Even a design based on so-called "high Tc" superconductors would not completely overcome these objections, and would introduce several new difficulties. See Fujiwara et al.

There have been more traditional approaches to detecting and quantifying the magnetic particles. These have involved some form of force magnetometry in which the sample is placed in a strong magnetic gradient and the resulting force on the sample is measured, typically by monitoring the apparent weight change of the sample as the gradient is changed. An example of this technique is shown in U.S. Pat. Nos. 5,445,970 and 5,445,971 to Rohr. A more sophisticated technique measures the effect of the particle on the deflection or vibration of a micromachined cantilever. See Baselt et al., A Biosensor based on Force Microscope Technology, Naval Research Lab., J. Vac Science Tec. B., Vol 14, No.2 (pg. 5) (April 1996). These approaches are all limited in that they rely on converting an intrinsically magnetic effect into a mechanical response. This response must then be distinguished from a large assortment of other mechanical effects such as vibration, viscosity, and buoyancy.

There would be important applications for an inexpensive, room-temperature, desktop instrument which could directly sense and quantify very small amounts of magnetic particles.

SUMMARY OF THE INVENTION

Broadly speaking, the present invention provides a method and an apparatus for directly sensing and measuring very small accumulations of magnetically susceptible particles, e.g., magnetite, and consequently, their coupled substances of interest.

The magnetic particles or beads are coupled by known methods to analyte particles, thereby providing magnetic sample elements or magnetic bound complexes. A well-defined pattern of the magnetic sample elements is deposited on a surface on a holder. The surface may be flat. A high-amplitude, high-frequency magnetic field is then applied to excite the particles in the sample. The field causes the particles to behave as a localized dipole oscillating at the excitation frequency. The fields from the sample are closely coupled to a sensor, such as an array of inductive sensing coils, which may be fabricated in a gradiometer configuration. This configuration makes the sensing coils mostly insensitive to the large, uniform field that is used to excite the sample. Moreover, the geometry of the coils is designed to match the spatial pattern of the sample so as to provide a large response that varies distinctively with the relative positions of the sample and coils.

The voltage induced across the sensor is carefully amplified and processed by phase-sensitive detection. An inductive pickup from the drive field itself may serve as the reference signal to the phase detector circuit. The output of the phase detector is further filtered and digitized.

The signal amplitude is modulated by moving the sample with respect to the sensor. This allows the rejection of signals due solely to imbalance of the sensor, non-uniformity of the drive field, cross-talk in the circuitry, or any other source of apparent signal which is not due to the sample itself. The digitized shape of the signal amplitude with respect to the sample position is compared to the theoretical response shape using appropriate curve-fitting techniques, providing a very accurate estimate of the magnetic content of the sample in the face of inherent instrument noise and drift.

BRIEF DESCRIPTION OF THE DRAWINGS

The object, advantages and features of this invention will be more clearly seen from the following detailed description, when read in conjunction with the accompanying drawings, in which.

DETAILED DESCRIPTION

Figure 1:
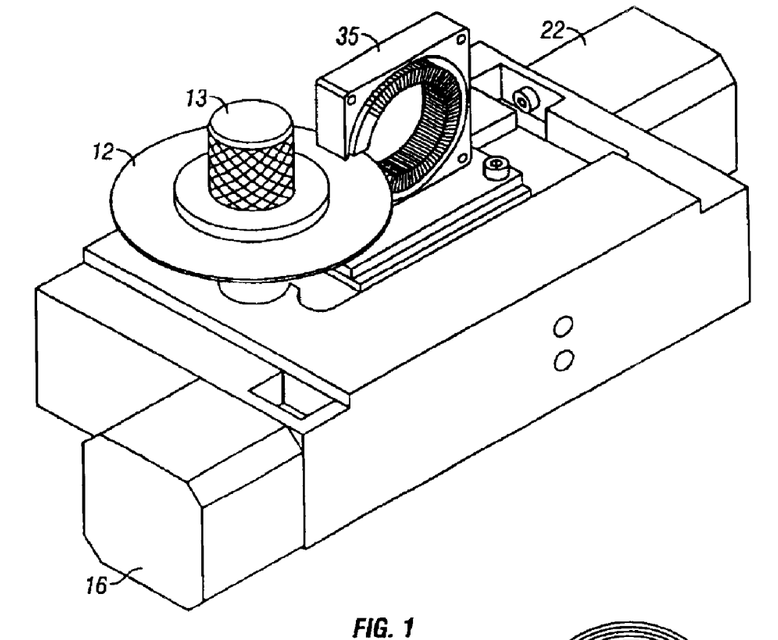
FIG. 1 is a perspective view of a desktop version of an embodiment of the present invention.
Figure 3:
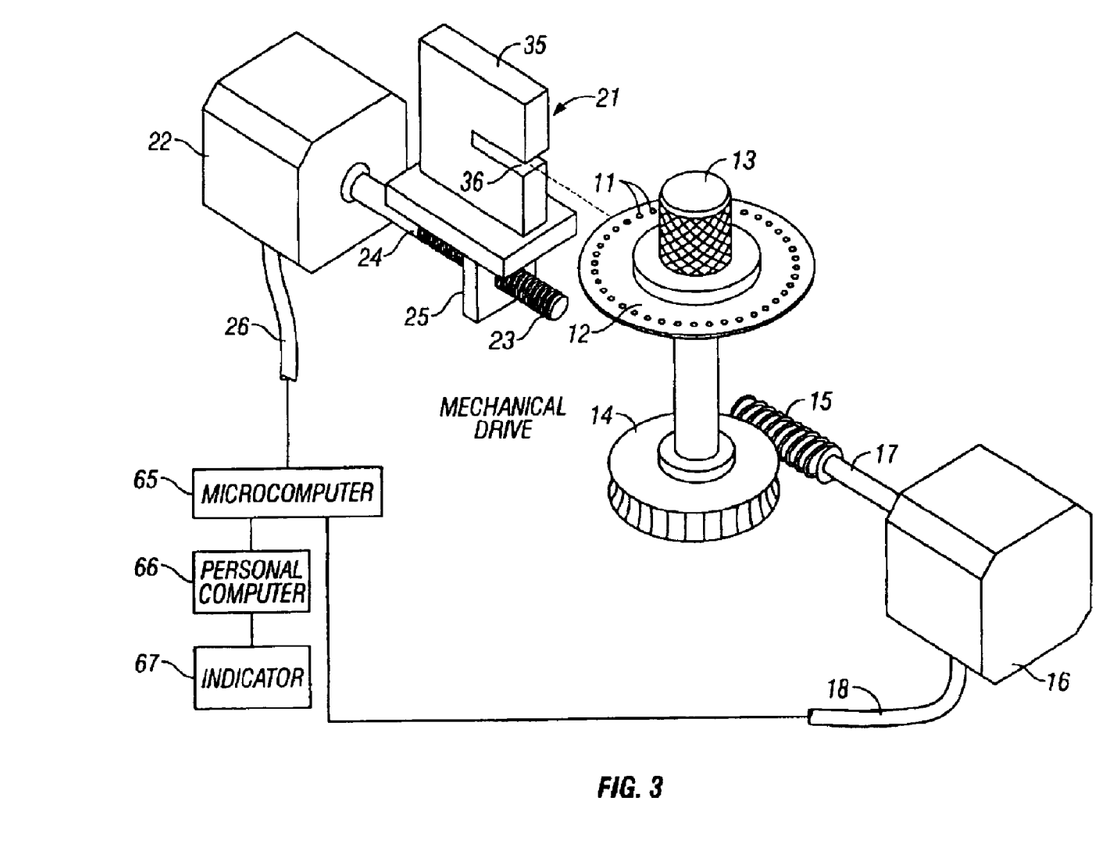
FIG. 3 is a mechanical schematic perspective view of the embodiment of FIG. 1.

Referring now to the drawing, and more particularly to FIGS. 1 and 3 thereof, there is shown a preferred embodiment of the invention.

I. Reader Module

The reader module includes several distinct subsystems. These include: a sample holder with a motion control. The magnetic bound complex samples for measurement reside on the holder, and the same also provides the necessary relative motion within the system. A magnetizer or magnetic field source applies the excitation signals to the samples. Sensors, such as sensing coils, act as the signal pick-up for the signals generated in the samples. A drive circuit supplies the drive current to the coils of the magnetic field source. An amplifier/phase detector/digitizer is coupled to the sensor to receive and process the output signals therefrom. A microcomputer chip provides two-way communication between the external personal computer (PC) and the reader module.

A. Sample Motion Control

Magnetic particles are coupled to analyte or target particles by conventional methods to create magnetic bound complex samples. The analyte particles may include atoms, individual molecules and biological cells, among others. It is noted here that the terms "target particle" and "analyte particle" are used substantially interchangeably. It is further noted that the term "target" is not intended to be limited to the definition of that term as used in the field of DNA recombinant technology.

The magnetic bound complex samples are deposited in accumulations of several to several hundred particles at a number of predetermined positions 11 near the perimeter of a sample holder, such as disc 12 (FIG. 3). Other sample holders which may be substituted include lateral flow membranes, plastic strips, or holders employing lateral flow but without membranes. An embodiment employing lateral flow membranes is described in more detail below.

Another type of sample holder may employ microfluidics. A microfluidics system may have a sample sensing chamber and appropriate channeling to move a sample in or out of the sensing chamber using variations in pressure. For example, referring to FIG. 9, a microfluidic system 151 is shown having an inlet channel 152. The inlet channel 152 is connected to a mixing chamber 164. A number of reagent chambers 154, 156, and 158 may be provided to hold various chemicals or reagents. As described below, they may also hold magnetically susceptible particles if desired. Near the periphery, or elsewhere, a sample analysis chamber 166 may be located. The location of this chamber is a predefined location and is where the sample magnetic measurement would occur. Accordingly, the sample holder must be configured to allow this chamber to be accessible to the sensor and the magnetic field source. Otherwise, the magnetic measurement may proceed as described elsewhere in this specification. Further processing may occur after the magnetic measurement. For this reason, a measurement chamber 168 is provided, which may also have its own reagent chamber 160. More reagent chambers may be provided if desired. An optional outlet or exit channel 162 may be provided. Such channels may not be necessary if the device is only a single-use device. Not shown in this figure for convenience but which may also be provided are various pressure inlets and valves which allow analyte particles, magnetically susceptible particles, and reagents to be shuttled around from chamber to chamber.

Figure 9:
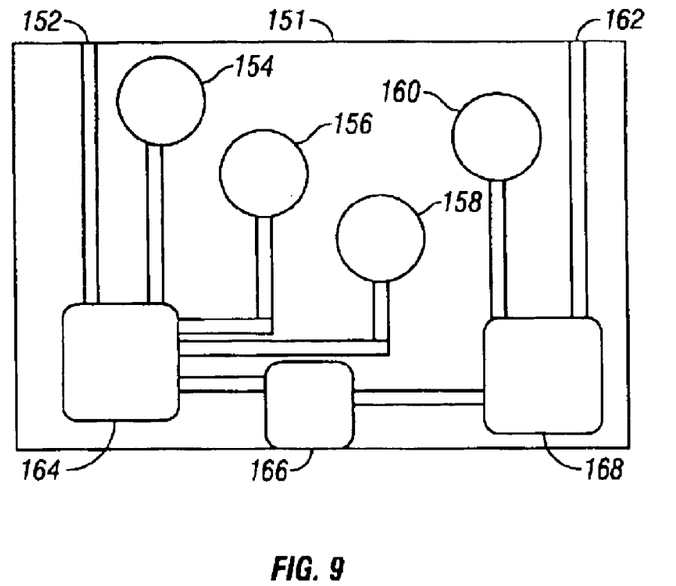
FIG. 9 is an embodiment of a microfluidic sample holder which may be used in an embodiment of the present invention.

Analyte particles may be quantitatively measured via measuring their bound magnetically susceptible particles. In the microfluidic system, the samples may be introduced via the inlet channel as combinations of analyte and magnetically susceptible particles. Alternatively, the analyte particles may be introduced via the inlet channel and the two may be combined and mixed in the mixing chamber 164.

Variations of this system may be manyfold. For example, the sensor may be located directly on the microfluidic chip to match the region of analysis especially well. In another variation, a different parameter on the chip may be varied at the same time or at a different time, such as temperature. Temperature control means may be located on the chip or outside of the chip, such as in the case of laser heating within the mixing chamber. Such a system requires an optical window, as would be understood. Other parameters which may be varied may be anything that affects the presence or property of the magnetic tag, i.e., the magnetically susceptible particle, or its binding to the analyte particle.

The ways the bound complexes may be adhered to the predefined spots on the disc are known and may employ standard technology. The disc is mounted on an axial shaft 13 which extends downwardly to a toothed wheel 14. An appropriate rotational device, such as a stepper motor 16, has a shaft 17 extending therefrom with a worm gear member 15 at the distal end thereof. The motor provides controlled rotary motion of disc 12 pursuant to signals applied from a PC 66 through a number of wires 18. Of course, wireless coupling between the PC and the system of the invention could be used if desired.

In one preferred embodiment, as presently contemplated, disc 12 is about 47 mm in diameter and about 0.25 mm thick. It may be made of glass, plastic or silicon, for example. Its thickness range, for practical functional purposes, would be about 0.1 mm to about 1.0 mm.

In the case where the sample holder is a lateral flow membrane, the sample holder may be made partially porous so that passage of the analyte particles through the porous portion of the holder may be another parameter to be varied. In this case, the magnetically susceptible particles may be bound to the porous sample holder. For example, passage of the analyte particles through a porous portion of a holder may likely depend on the mass or size of the particles. Thus, the location of the particles within the porous portion may be mass-dependent or size-dependent. As the analyte particles pass through the porous sample holder, they may bind preferentially and in a predetermined manner to the bound magnetically susceptible particles. The bound samples, containing analyte particles combined with magnetically susceptible particles, may then be measured magnetically using the device embodied herein. The porous portion of the holder may be replaced with, e.g., a filter as is known in the art. Such filters may be chosen to provide a suitable mass- or size-dependency according to the requirements of the process.

Figure 7:
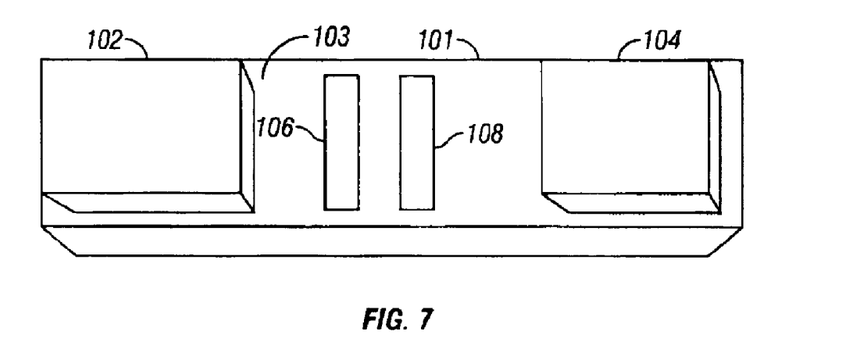
FIG. 7 is an embodiment of a lateral flow membrane sample holder which may be used in an embodiment of the present invention.

For example, referring to FIG. 7, a lateral flow membrane 101 is shown. Analyte particles may be flushed into a release pad 102 where they are released into a flow membrane 103. The particles may then flow by capillary action down the membrane and past a test line 106 on which bound magnetically susceptible particles are located. A control line 108 may also be provided. Finally, an absorbent pad 104 may be located downstream if desired to collect the unbound analyte particles.

In operation, the test line may include colloidal iron particles coated with a material that specifically binds to a material in the analyte of interest. In this way, the test line collects analyte particles preferentially. The control line 108 may have a known amount of colloidal iron for calibration or other such purposes. It should be clear that such a lateral flow membrane may be replaced with, e.g., a gel electrophoresis test area. In this case, of course, the samples are not immobilized but may be moving past the sensing area.

The sample holder may also employ a reference device, such as a bar code 167, to provide a unique machine-readable tag to identify or locate an individual region or regions and the assay(s) that are associated thereby. The reference device may spatially index the location of an individual region or regions of analysis. The reference device gives a convenient way to identify a sample of magnetic complex material. Besides bar codes, the reference device may alternatively employ a magnetic strip 169, a microchip, an optical reference, and so on. The reference device may be optically aligned with its corresponding sample for ease of reference.

The computer/CPU may read the reference information along with the magnetic (assay) signal and then display and store the assay results in the appropriate context. For example, an assay to measure the presence of *e. coli* would likely have results displayed in a different form than an assay testing for the presence of binding of oligonucleotides. Since the substrate may be prepared specifically for each kind of assay, this information can be encoded on the substrate as a bar code or using one of the techniques described above.

In this particular exemplary embodiment, motor 16 rotates wheel 14, which is connected to disc 12 by shaft 13, through a 120-tooth worm gear reduction. Of course, rotational drives having different particulars could also be employed.

A magnetic field source 21 may be moved linearly with respect to disc 12 by a rotational device, such as a stepper motor 22, having a 40 turn-per-circle lead screw 23 on a motor shaft 24. A boss 25 is configured with a hole having internal threads to which the spiral lead screw threads are coupled. The control signals are applied from microcomputer 65 to motor 22 through a number of wires 26. Again, the specifics of the rotational drive are set out here as an example only. Other appropriate elements having different characteristics could also be used.

For example, while the above system describes a situation where the magnetic field source is moved linearly with respect to the sample holder, another embodiment may be used in which the sample holder is moved relative to the magnetic field source. In this latter embodiment, the sample holder may be mounted to a shaft and mechanical drive system similar to the drive system shown in FIG. 3. The drive system may move the sample holder into the gap of the magnetic field source in a controlled manner.

Numerous types of drive systems may be employed. These include stepper motors, screw and motor arrangements, hydraulics, magnetic drives, configurations in which a human operator physically moves the sample holder relative to the magnetic field source and relative to the sensor, pressure drives, pinch rollers, conveyor systems, etc.

The above describes the motion of the sample holder from a location in which samples may be loaded, such as on a disc, to a location near the magnetic field caused by the magnetic field source. Another motion that occurs in the system is the movement of the sample holder past the sensor. Various motions may be caused to accommodate this. For example, two-dimensional motion may be accommodated between the sensor and the sample holder. In the embodiment of FIG. 3, one degree of freedom motion (e.g., along an arc of a circle) is shown using motor 16. The drive system of motor 22 may also be employed to translate the sensor along another degree of freedom. Alternatively, another motor may be used to move the sample holder 12 along a similar degree of freedom. Finally, it should be noted that, by using appropriate gearing, the same motor may be used to provide any combination of the above or different motions.

In other exemplary embodiments, the drive system may include a pinch roller which grasps a plastic strip on which a sample is disposed, moving the same past the sensor in a controlled fashion. Such an embodiment may be particularly useful where the sample is placed in a strip on a plastic card similar to a credit card, which is then "grabbed" by a device similar to that used in ATM machines. Of course, the drive system may also be any of the systems described above as well as other alternate systems.

B. Magnetic Field Source

Figure 4:
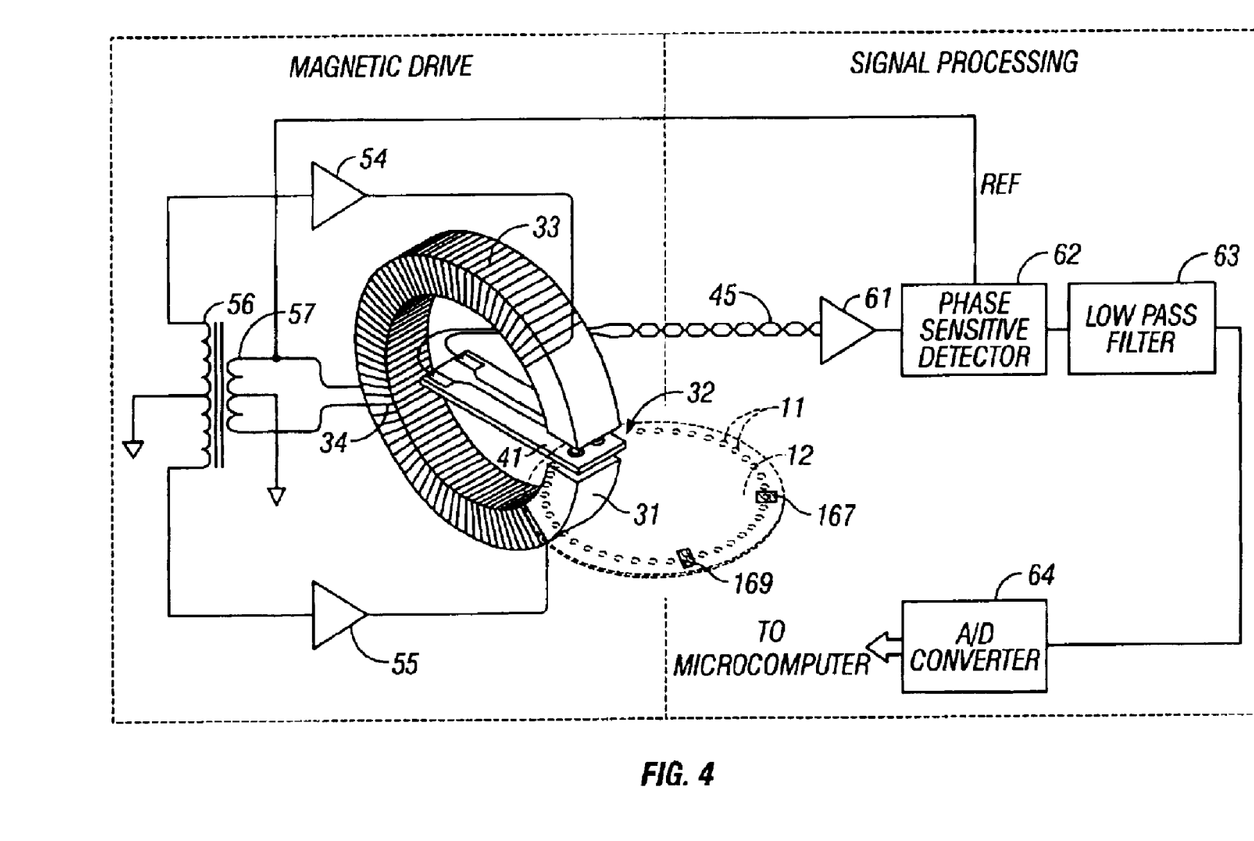
FIG. 4 is an electrical schematic diagram of the embodiment of FIG. 1.

Referring to FIG. 4, a ferrite toroid core 31, which is about 30 mm in diameter in the particular embodiment being described, is formed with a gap 32, which is about 1.5 mm wide. A drive coil 33 is wound as a single layer over about 270 of toroid 31, symmetric with respect to the gap. A feedback loop 34 encircles the toroid body at a location about 180 from (opposite) the gap. Loop 34 may be outside of coil 33 or between coil 33 and the toroid core. It may include a few or many turns, as necessary and appropriate for the feedback function. The purpose of the feedback loop is to sense or represent the field in gap 32 and enable the signal processing or output circuit to self-correct for variations such as temperature drift. This loop is used to enhance precision and is not essential to proper operation of the system.

Figure 8:
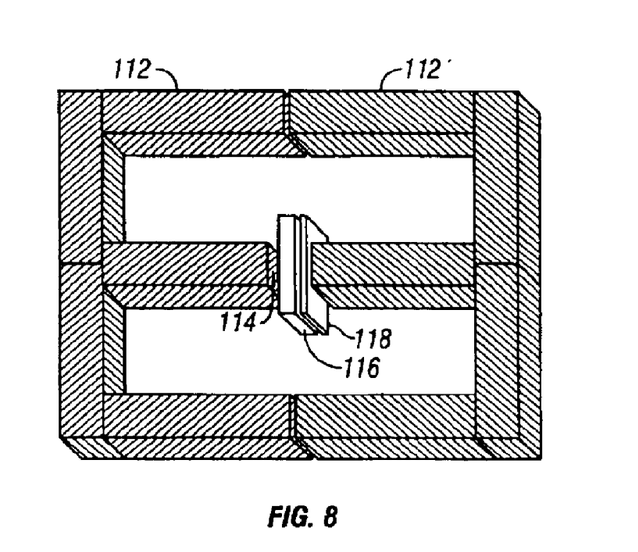
FIG. 8 is an E-core magnet system which may be used as the magnetic field source according to an embodiment of the invention (note that no drive coils are shown for clarity)

Various other magnetic field sources may also be used. For example, while most all employ electromagnets, the electromagnets may be in the form of, e.g., toroids or so-called "E-core"s which are magnets employing the shape of an "E" (see FIG. 8). In E-cores, the middle segment of the "E" is made somewhat shorter than the outer segments. Referring to FIG. 8, two E-cores 112 and 112' are placed with their open sides facing each other. The shorter middle segments then define a small gap 114 therebetween. A sample on, e.g., a plastic strip 116 may then be situated in this small gap. The sensor used to measure the oscillation of the magnetizations may be on a separate substrate 118 also located in the small gap or may alternatively be disposed on the end of one or both of the shorter middle segments. In any of the embodiments, in fact, the sensor may be disposed on a magnetic pole piece or other such element that forms a perimeter of the gap. In this way, the unit may be made more modular and the coil placement more uniform and consistent.

Figure 10:
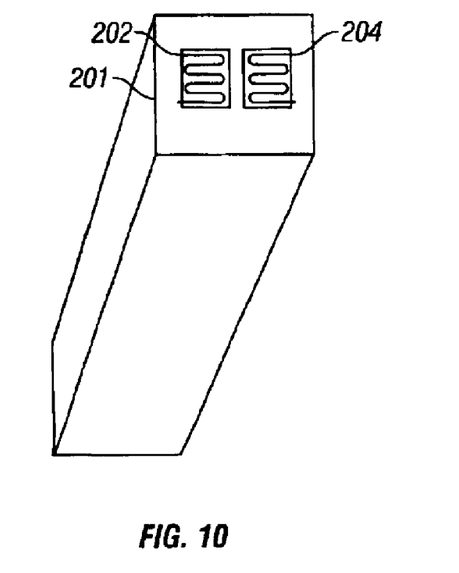
FIG. 10 is an embodiment of a single magnet pole piece with attached sensor which may be used in an embodiment of the present invention.

In other embodiments, no gap is needed at all. Referring to FIG. 10, a single magnetic pole piece 201 may be situated with a sensor disposed thereon or disposed on a separate strip. In FIG. 10, the sensor is shown as two sensing coils 202 and 204. The pole piece can alternate the magnetic field, and the sensor can measure the oscillating magnetizations as above.

Referring back to FIG. 3, the toroidal magnetic field source assembly is mounted in insulative housing 35, which may be formed from fiberglass. Housing 35 has a slot 36 corresponding to the position of gap 32. This slot/gap is shaped and configured to selectively receive the edge of rotatable disc 12, and provides space for the sensing coil substrate, which is described in detail below.

C. Sensors

A sensor is used to measure the magnetic field strength of the samples. In this embodiment, the method used is AC susceptibility. A number of types of sensors may be employed. In the embodiments below, sensing coils connected in a gradiometer configuration are described. It should be noted that the gradiometer configuration is not necessarily required; moreover, other types of sensors may be used. These sensors may include Hall sensors, GMR sensors, or other such sensors capable of measuring magnetic field strength or magnetic flux.

Figure 2:
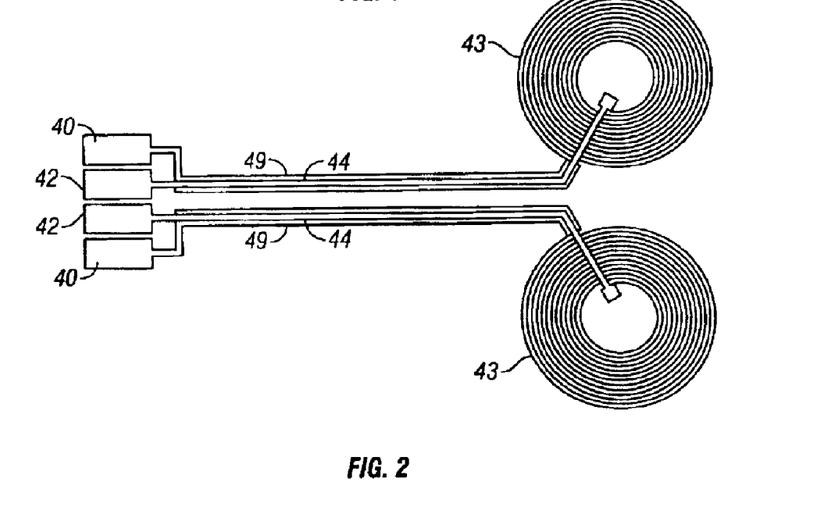
FIG. 2 is an enlarged plan view of an embodiment of the sensor, showing sensing coils in the embodiment of FIG. 1.
Figure 4A:
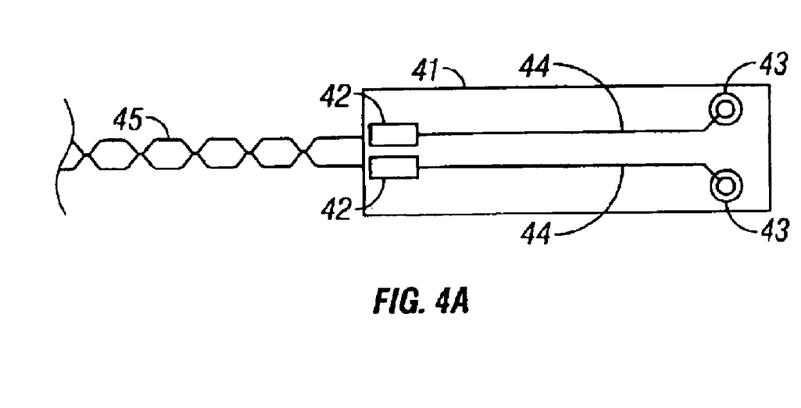
FIG. 4A is an enlarged plan view of the substrate holding the sensing coils of FIG. 1.

With particular reference now to FIGS. 2, 4 and 4A, insulative substrate 41 is disposed in slot 36 in housing 35 and extends into gap 32. Bonding pads 40, 42 are provided at a proximal end of substrate 41 and a sensor, in particular sensing coils 43, is mounted adjacent a distal end of substrate 41. Preferably the substrate is made of sapphire or silicon and the sensing elements are thin film copper coils. Standard thin film fabrication techniques can be used to construct the substrate and sensing coils, where the leads to and from each coil are on separate different layers. For example, incoming traces 49 may be laid on the substrate surface by standard photolithographic processing methods, a layer of sputtered quartz may then cover the incoming leads, then coils 43 and output leads 44 are similarly applied and a protective layer of quartz may then be added on top. The usual means for connecting between the layers would be used.

The sensing coils, which are connected in series opposition creating a gradiometer configuration, are connected to bonding pads 40 and 42 by conductive traces 44 and 49, and thence to signal processing circuitry by twisted-pair wires 45. The twisted pair arrangement is employed to assist in reducing stray signal or interference pickup.

In the spiral form shown in FIG. 2, the coil traces may be about 5 microns in width with about a 10-micron pitch between spiral traces. The thickness of the sensing coil traces may be about 1 micron. The diameter of each completed coil is about 0.25 mm.

Figure 4B:
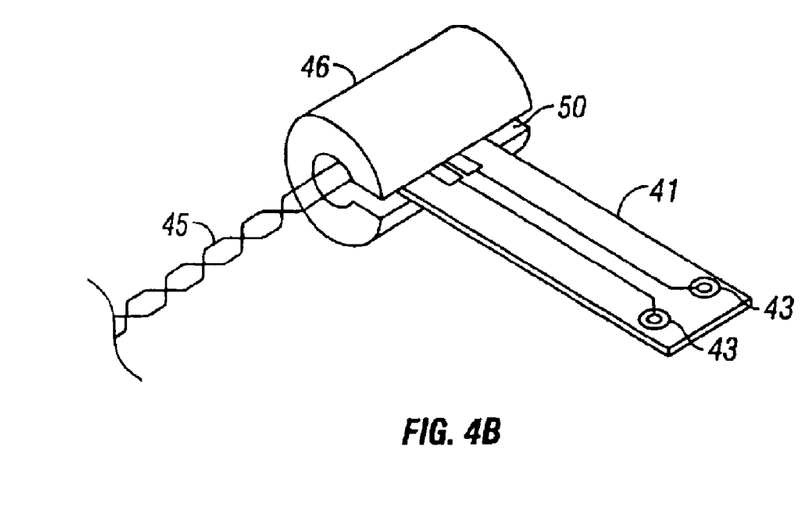
FIG. 4B is a perspective view of a metal shield for the connection end of the substrate.

By making substrate 41 relatively long and narrow, bonding pads 40, 42 are relatively far away from the toroid gap, which helps minimize stray pickup in soldered leads 45. Metal shield 46 (FIG. 4B) may be employed around the bonding area to further contribute to the reduction of stray signals or interference pickup. The shield is essentially a short piece of a thick-walled cylinder, typically formed of copper. The shield provides electrical shielding and facilitates mechanical handling, but is not essential to operation of the embodiment of the invention. The connection (proximal) end of the substrate is slid into slot 50 after the wire connections are made.

Figure 5:
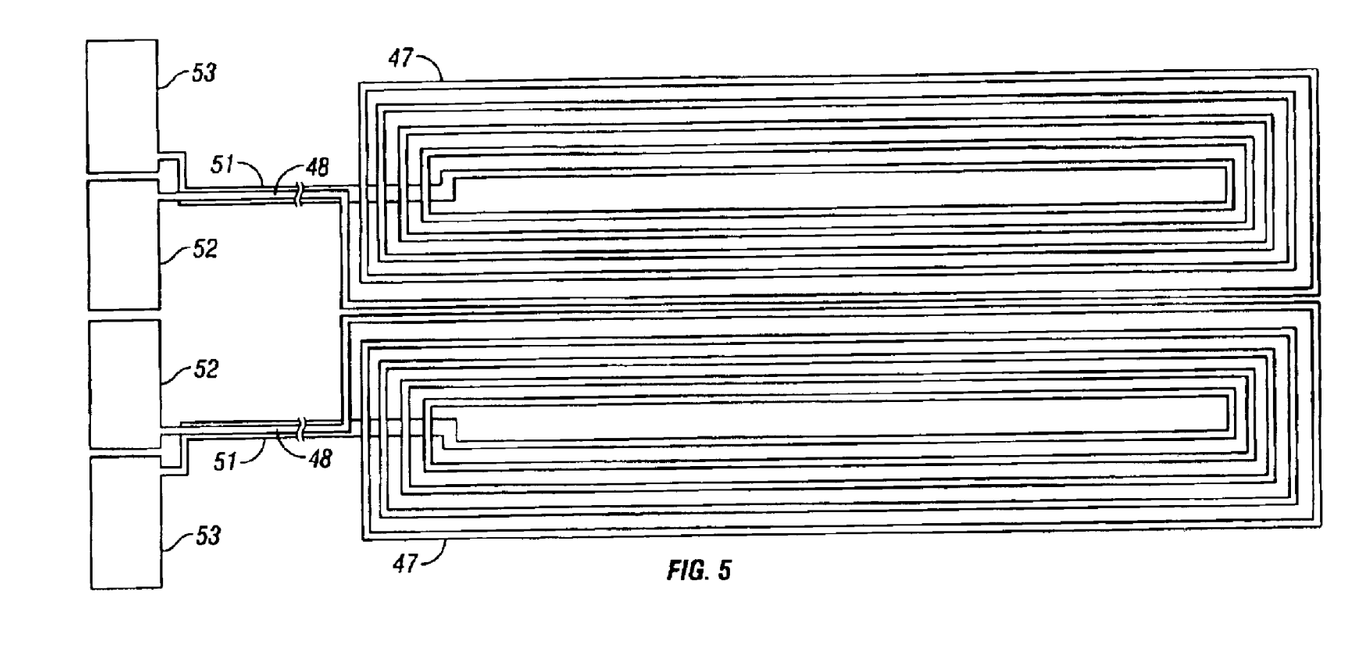
FIG. 5 is an enlarged plan view of an alternative embodiment of the sensing coils of the embodiment of FIG. 1.

An alternative embodiment of the sensing coils is shown in FIG. 5. The planar configuration of coils 47 is an elongated rectangle. The trace dimensions are about the same as for the FIG. 2 coils and the composite coil width is also about 0.25 mm. The coil length is about 1–2 mm and the coils are connected to bonding pads 52, 53 by means of leads 48, 51.

In another alternative embodiment, two sets of coils may be used. One set of coils may be used as described above, to measure the magnetic moment of the sample. Another set of coils may be employed within the same substrate as a reference set of coils. This reference set of coils may be disposed, e.g., on the side of the substrate opposite that of the sample set of coils. In any case, the reference set of coils is disposed far enough from the sample that the effect of the sample magnetic moment is not detected by the reference set of coils. The reference set of coils is then used to measure the strength of the signal from an analysis region containing a predetermined amount of magnetic material or reference analyte. By comparison of the magnetic field detected by the sample set of coils with the magnetic field detected by the reference set of coils, an even more accurate measurement of the sample magnetic moment may be made. To provide another reference, a magnetic standard may be employed as one of the samples. When such a standard sample is measured, the results may be used to calibrate the system for future or previous measurements. This calibration may significantly help to reduce noise in the system. Auto-calibration may also be employed with such a system, using the differential between signals, to zero the signal.

D. Drive Circuit

The magnetic drive circuit, shown at the left side of FIG. 4, is built around a pair of high-current, high-speed operational amplifiers 54, 55. With the power provided by transformer primary winding 56, the amplifiers can provide in excess of about one ampere of drive current to magnetizing or drive coil 33 at about 200 kHz. This drive circuit is highly balanced to minimize common-mode noise pickup in sensing loops or coils 43, 47.

Small secondary winding 57 coupled to loop 34 around the magnetizing coil provides a feedback voltage to operational amplifiers 54 and 55 to sustain oscillations at a well-regulated amplitude and frequency. This secondary winding 57 also provides an optimum reference signal for the phase-detector circuitry, described below.

This embodiment describes an alternating field as the driving source for the complex of magnetic and analyte particles. In a separate embodiment, the driving source may be non-sinusoidal, e.g., may be a field pulse or a square wave. A variety of other such waveforms may also be used.

E. Amplifier/Phase Detector/Digitizer

A low-noise integrated instrumentation amplifier is the basis for this circuitry, although somewhat better noise performance could be obtained using discrete components. Amplifier 61 is transformer coupled to the sensing coils in order to reduce common-mode noise signals and to facilitate a convenient way to null out imbalance in the magnetic field source and in the sensor. The transformer coupling is conventional, is located in amplifier 61, and is not specifically shown in the drawing. In an alternative embodiment, amplifier 61 may be replaced by or supplemented with a preamplifier disposed on the substrate. In other words, substrate 41 may have patterned thereon a preamplifier to modify the signals from the sensor prior to the phase-sensitive detection step. Phase sensitive detector 62 is also designed around a special purpose integrated circuit. Phase sensitive detector 62 may be a phase-locking device or alternatively any other type of phase-sensitive device. The output of the phase detector is applied to low-pass filter 63 and is then digitized in A/D converter 64. The converter may be a high resolution, 20-bit sigma-delta converter, for example. Such a converter chip has adequate hum rejection at both 60 and 50 Hz, which proves to be very helpful in maximizing the sensitivity of the instrument. It is an off-the-shelf item, available from several manufacturers.

F. Microcomputer

Microcomputer 65 includes a microprocessor chip, such as a Motorola HC11, and has a built-in port which supports two-way serial communication to PC 66 by plugging into the serial port of the PC. It also has specialized ports for communication with serial A/D converter 64 and stepper motors 16 and 22. A simple command language programmed directly into microcomputer 65 allows the PC to send commands and receive responses and data.

Microcomputer 65 may also perform many of the functions previously described above. For example, microcomputer 65 may be equipped with a phase-sensitive device of its own, such as a digital lock-in. Such a microcomputer 65 may acquire the signals, separate data from noise, and display the results.

G. Human Interface

The PC provides the operational command for the system. The PC runs the system through an RS-232 interface, e.g., from the microcomputer. The PC provides a display of the results of the measurements. The display may be, e.g., a computer monitor display or any other form of computer-assisted readout.

II. Operation of the System

In a relatively straightforward and known manner, a well-defined dot or pattern of the magnetic particle complexes comprising the samples is deposited on disc 12 at one or more locations 11 near the periphery thereof. Pursuant to control signals from the PC, stepper motor 22 is energized to rotate lead screw 23 to move the magnetic field source assembly towards sample disc 12. When a sample position 11 near the peripheral edge of disc 12 is aligned with a sensor such as sensing coils 43, 47 in the middle of toroidal gap 32, stepper motor 22 stops and a high amplitude (1 ampere, for example), high frequency (200 kHz) signal is applied to toroidal drive coil 33. Again, while sensing coils are described below, it should be understood that a variety of sensors may be employed. A signal from PC 66 then energizes stepper motor 16 to rotate the disc and thereby move the sample dot past the sensing coils. The high amplitude, high frequency magnetic field in gap 32 thereby excites the magnetic particles of the sample in the gap. The applied current is intended to drive the toroid to saturation, resulting in the field in the gap have a magnitude of about 1000 oersted. The particles then oscillate magnetically at the excitation frequency, behaving as a localized dipole. Given the close physical proximity of the magnetic particles to the sensing coils, the magnetic fields from the sample are closely coupled to the gradiometer configured sensing coils. Because of the gradiometer configuration of the sensing coils, the output of the sensing coils due to the large, uniform excitation field is substantially null or zero. In order to obtain the largest possible response, the geometry of the sensing coils is configured to match the spatial pattern of the samples. That is, the sample pattern dots are no larger than about 0.25 mm across. The response signal varies distinctively with the relative position of the sample and the coils.

Figure 6:
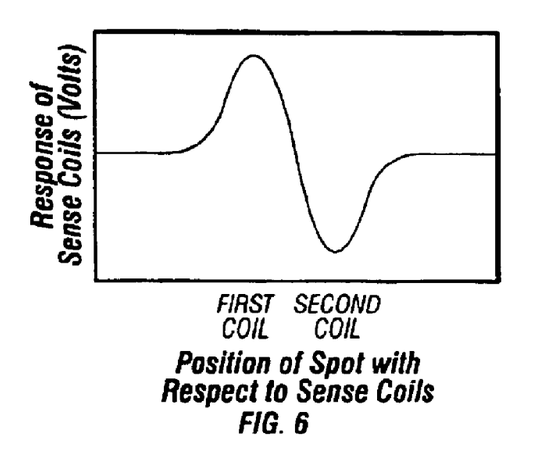
FIG. 6 is a signal waveform of the output of the sensing coils versus the position of the magnetic material.

The signal from the sensing coils in the presence of the drive field and in the absence of a sample may serve as the reference signal to the signal processing portion of the system. As the sample moves past one sensing coil and then the other, the phase of the coil output signal reverses by 180 as shown in FIG. 6, thereby providing a very powerful detection technique. As shown in FIG. 6, the output may be shown as the response of the sensing coils versus the position of the sample with respect to the sensing coils. The induced voltage is amplified by amplifier 61 and processed by phase detector 62. That signal is filtered and digitized and passed to the PC through microcomputer 65 to provide the output signals to the PC. Indicator 67 may be any type of useable device to provide information to the system operator. Indicator 67 could be a visual indicator, conveying information numerically or graphically, or could also be a variety of lighting systems, audible indicators, or any combination of these or other possible indicators.

The output signal amplitude is modulated by moving the sample with respect to the array of the sensing coils. This permits rejection of signals due solely to system and external inputs and not due to the sample itself. The digitized shape of the signal amplitude with respect to sample position is compared to the theoretical response shape stored in PC 66 using appropriate curve fitting techniques. These techniques may include phase-sensitive techniques or other techniques yielding similar results. The result of this operation is a very accurate estimate of the magnetic content of the sample to the exclusion of inherent instrument noise and drift.

While a preferred embodiment of the invention has been presented above, some alternatives should be mentioned. Two sensor coil shapes have been shown but numerous other configurations may be employed. Moreover, as indicated above, sensors may be used which are patterned directly on one or more of the magnetic field source pole pieces. Furthermore, other varieties of sensors could be employed besides the types of coils disclosed. For example, balance hall sensors may be employed. In appropriate configurations, these may yield a frequency independent signal. Other sensors which may be advantageously employed include giant magnetoresistance (GMR) sensors, SQUID sensors, magneto-resistance sensors, etc.

In other variations, the magnetic field source is shown as moving with respect to the sample disc, but the disc and coupled stepper motor could be configured to move with respect to the magnetic drive assembly if desired. The toroid core is shown with a rectangular cross section but other shapes are also feasible. As to the number of sample particles in a dot 11 on disc 12, by way of example, a 0.25 mm dot of sample elements could contain about 10 five-micron size magnetic particles, or about 1200 one-micron size particles.

Thus, in view of the above description, it is possible that modifications and improvements may occur to those skilled in the applicable technical field which are within the spirit and scope of the accompanying claims.

What is claimed is:

1. An apparatus for quantitative magnetic measurement of samples, each sample arranged in a predefined pattern and disposed in a sample holder, comprising:

a magnetic field source to apply a magnetic field to the sample, the magnetic field source defining a gap in which a sample holder is movably disposed;

a substantially flat magnetic field sensor to sense an induced magnetic moment from the sample and configured and arranged in a gradiometer configuration to substantially eliminate the contribution of the magnetic field source to the sensing, the magnetic field sensor having a sensing area substantially the same as the extent of each sample, the magnetic field sensor having an output to communicate output signals to provide quantity of the samples in the pattern, the magnetic field sensor disposed substantially within the gap of the magnetic field source.

* * * * *